United States Patent [19]

Matsuura et al.

[11] Patent Number: 5,153,339
[45] Date of Patent: Oct. 6, 1992

[54] PROCESS FOR SEPARATION OF NAPHTHOQUINONE AND PHTHALIC ACID

[75] Inventors: Ryo Matsuura, Yamato; Tatsuyoshi Komatsu, Kamakura; Kenji Usui, Tokyo; Toru Sato, Kawasaki, all of Japan

[73] Assignee: Kawasaki Kasei Chemicals Ltd., Tokyo, Japan

[21] Appl. No.: 392,156

[22] Filed: Jun. 25, 1982

Related U.S. Application Data

[63] Continuation of Ser. No. 139,651, Apr. 14, 1980, abandoned.

[30] Foreign Application Priority Data

Apr. 25, 1979 [JP] Japan ............................. 54-51258

[51] Int. Cl.⁵ .................. C07C 46/10; C07C 50/12
[52] U.S. Cl. ................................. 552/296; 562/485; 562/486
[58] Field of Search ............ 260/396 R; 549/250; 552/296

[56] References Cited

U.S. PATENT DOCUMENTS 4,202,828  5/1980  Matsuura et al. ............... 260/396 R

FOREIGN PATENT DOCUMENTS 97558     4/1975  Japan .
54-98734  8/1979  Japan ............................ 260/396 R
928459    6/1963  United Kingdom .

*Primary Examiner*—Vivian Garner
*Attorney, Agent, or Firm*—Oblon, Spivak, McClelland, Maier & Neustadt

[57] ABSTRACT

Naphthoquinone having a purity of higher than 95% is separated from an aqueous slurry of naphthoquinone and phthalic acid prepared by contacting, with an aqueous medium, a reaction mixture gas containing naphthoquinone and phthalic anhydride formed by a catalytic vapor phase oxidation of naphthalene. An extraction of naphthoquinone is carried out with a chain or cyclic saturated hydrocarbon at 60° to 110° C. under the condition adjusting pH to 1.2 to 5 and substantially dissolving phthalic acid in the aqueous phase and leaving resinous materials as a bottom.

6 Claims, 2 Drawing Sheets

PROCESS FOR SEPARATION OF NAPHTHOQUINONE AND PHTHALIC ACID

This is a continuation of application Ser. No. 139,651, now abandoned, filed Apr. 14, 1980.

BACKGROUND OF THE INVENTION

1. Field of the Invention

The present invention relates to a process for a separation of naphthoquinone and phthalic acid. More particularly, it relates to a process for a separation of naphthoquinone at high purity from an aqueous slurry containing 1,4-naphthoquinone (hereinafter 1,4-naphthoquinone is referred to as naphthoquinone) obtained by washing, with water, a reaction mixture gas obtained by a catalytic vapor phase oxidation of naphthalene.

2. Description of Prior Arts

It has been proposed to separate naphthoquinone and phthalic acid from an aqueous slurry obtained by washing, with water, naphthoquinone and phthalic anhydride by contacting an aqueous medium, with a reaction mixture gas obtained by a catalytic vapor phase oxidation of naphthalene, wherein the naphthoquinone is extracted from the aqueous slurry with an aromatic hydrocarbon solvent such as xylene to separate a naphthoquinone solution from an aqueous solution of phthalic acid (See Japanese Examined Patent Publication No. 20026/1978.).

It has been also proposed in Japanese Examined Patent Publication No. 9209/1978 to separate an insoluble naphthoquinone crystal by adding a base to an aqueous medium obtained by washing, with water, the reaction mixture gas obtained by the catalytic vapor phase oxidation, to dissolve phthalic acid as a mono-salt of phthalic acid. Thus, the purity of naphthoquinone obtained by these known processes is too low. In the former process, polycondensed quinones and resinous materials contained in the aqueous slurry of naphthoquinone and phthalic acid obtained by washing, with water, the reaction mixture gas obtained by the catalytic vapor phase oxidation of naphthalene, are dissolved into the aromatic hydrocarbon used for the extraction, whereby the solution of naphthoquinone contains the impurities.

In the latter process, as described in the specification especially the examples, the impurities of the polycondensed products and resinous materials which are insoluble to the aqueous phase is included at a ratio of about 5%, in naphthoquinone crystal and naphthoquinone having high purity cannot be obtained.

Naphthoquinone is a remarkably important industrial compound as an intermediate of dyes and agricultural chemicals. It has been required to produce naphthoquinone having high purity, however, it has not been succeeded to produce naphthoquinone having high purity by an industrially advantageous process from the reaction mixture gas obtained by the catalytic oxidation of naphthoquinone.

The inventors have studied to obtain naphthoquinone having high purity from the reaction mixture gas formed by the catalytic vapor phase oxidation of naphthalene. As a result, it has found that the impurities such as polycondensed products and resinous materials are not substantially dissolved in the saturated hydrocarbon solvent phase, but only naphthoquinone is selectively extracted into the saturated hydrocarbon solvent phase to easily separate the impurities such as the polycondensed products and the resinous materials as the insoluble materials by using the saturated hydrocarbon solvent in the extraction of naphthoquinone from the aqueous slurry containing naphthoquinone and phthalic acid, the pH of which is adjusted to the specific range so as to prevent the polycondensation of naphthoquinone.

SUMMARY OF THE INVENTION

It is an object of the present invention to provide a process for separating naphthoquinone having a purity of higher than 95% from a reaction mixture formed by a catalytic vapor phase oxidation of naphthalene, without an additional purification such as a recrystallization.

The foregoing and other objects of the present invention have been attained by separating naphthoquinone having a purity of higher than 95% and phthalic acid from an aqueous slurry prepared by contacting a reaction mixture gas containing naphthoquinone, phthalic anhydride and sulfuric acid formed by a catalytic vapor phase oxidation of naphthalene with an aqueous medium, by adjusting the pH of the aqueous slurry to 1.2 to 5 and extracting the aqueous slurry with a chain or cyclic saturated hydrocarbon at 60° to 110° C. under the condition of substantially dissolving phthalic acid in the aqueous phase thereby separating a naphthoquinone solution phase, an aqueous phthalic acid solution phase and a resinous material phase.

BRIEF DESCRIPTION OF THE DRAWING

In FIG. 1; abscissa: temperature (°C.); ordinate: polycondensation percent of naphthoquinone (mole %); in FIG. 2: abscissa: pH; ordinate: polycondensation percent of naphthoquinone (mole %).

DETAILED DESCRIPTION OF THE PREFERRED EMBODIMENTS

The catalytic vapor phase oxidation of naphthalene can be carried out in any conventional processes. In usual, the reaction is carried out by using an oxygen containing gas such as air in the presence of a vanadium pentaoxide-potassium sulfate type catalyst to obtain a reaction mixture gas containing naphthoquinone and phthalic anhydride as main components and a small amount of maleic anhydride. The starting material of a crude naptalene contains sulfur compounds such as thionaphthene and such sulfur compounds are oxidized to form sulfuric anhydride and/or sulfuric acid which are included in the reaction mixture gas. The reaction mixture gas is cooled to about 200° C. and is brought into contact with an aqueous medium in a scrubber to collect naphthoquinone and phthalic acid in an aqueous slurry. In the operation, maleic anhydride and sulfuric anhydride are collected by dissolving them as maleic acid and sulfuric acid. The aqueous medium is separated from naphthoquinone and phthalic acid and is reused by recycling into the scrubber.

When a bubbling column is used for forming an aqueous slurry from the reaction mixture gas, the reaction mixture gas is fed into the aqueous medium (the aqueous slurry in the continuous operation) in the bubbling column and a part of the aqueous slurry is discharged and naphthoquinone and pthalic acid are separated and the filtrate (mother liquor) is recycled into the bubbling column. It is advantageous in an industrial operation to recycle the mother liquor obtained by separating naphthoquinone and phthalic acid, as the aqueous medium used in the process of the present invention. Water can be also used as the aqueous medium. When the mother liquor is recycled, the by-products of maleic acid and sulfuric acid are accumulated to decrease gradually the pH of the aqueous medium or the aqueous slurry. When such aqueous medium is reused, the polycondensation of naphthoquinone and other side reaction are performed at high degree by heating it in the step of washing the hot reaction mixture gas containing naphthoquinone and phthalic anhydride with water and extracting naphthoquinone with a solvent from the resulting aqueous slurry, whereby a polycondensation of naphthoquinone is resulted.

Figure 1:
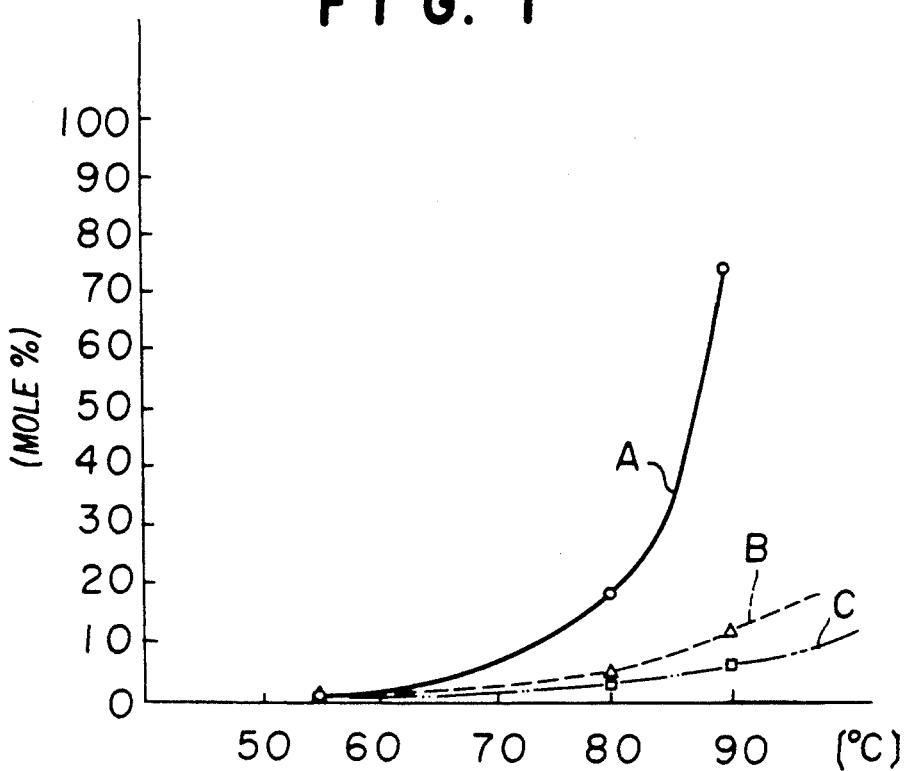
FIG. 1 is a graph for showing effects of a temperature to polycondensation percent of naphthoquinone in an aqueous solution of phthalic acid.
Figure 2:
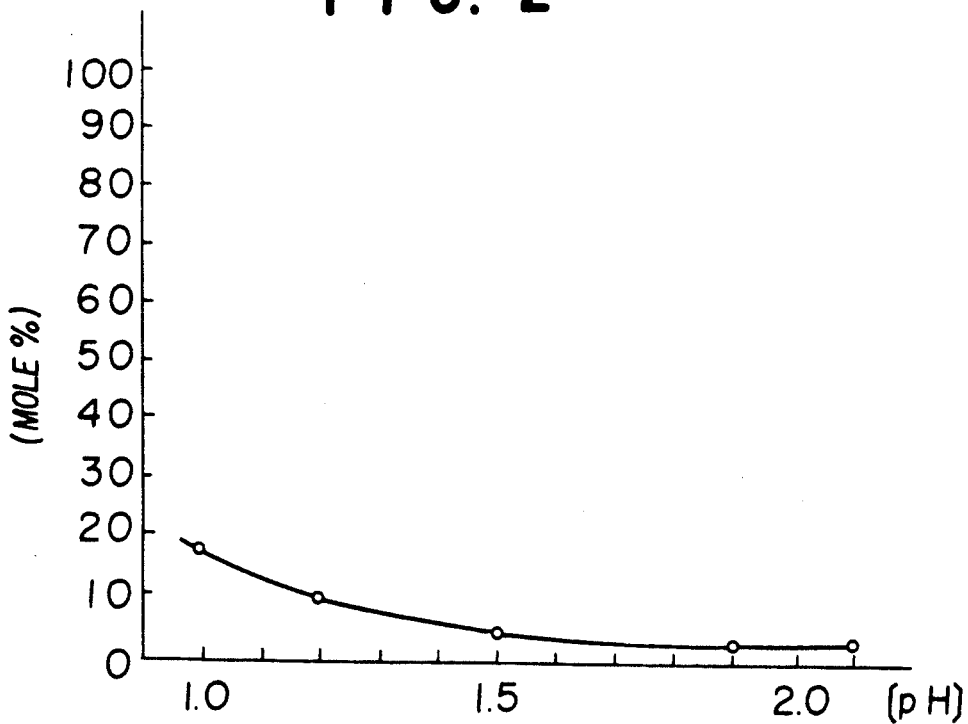
FIG. 2 is a graph for showing effects of pH to polycondensation percent of naphthoquinone in a treatment at 80° C. for 4 hours.

The effects of the temperature and pH to the polycondensation of naphthoquinone in an aqueous solution of phthalic acid are shown in FIGS. 1 and 2. In this test, an aqueous slurry containing 2.4 wt. % of naphthoquinone, 6.5 wt. % of phthalic acid, 1.2 wt. % of sulfuric acid and 1.4 wt. % of maleic acid is used as a test solution (pH: 1.0). In FIG. 1, the temperature (°C.) is plotted on the abscissa and the polycondensation percent of naphthoquinone (mole %) is plotted on the ordinate. The curves of polycondensation of naphthoquinone in each reaction at the temperatures shown as the abscissa for 4 hours are shown as the curve A for the pH non-adjusted test slurry; the curve B for the test slurry adjusting pH to 1.5; and the curve C for the test slurry adjusting pH to 2.1.

In FIG. 2, the polycondensation percent of naphthoquinone (mole %) is plotted on the abscissa and pH is plotted on the ordinate. The same test slurry of FIG. 1 is used to adjust pH by adding an aqueous solution of sodium hydroxide. The treatment is carried out at a treating temperature of 80° C. and the treating time was 4 hours in each pH.

It is found from FIGS. 1 and 2, when pH is less than 1.2 especially at higher than 60° C., the polycondensation of naphthoquinone is seriously caused. When the treatment is carried out at higher than 60° C., especially higher than 80° C., the polycondensation can be effectively prevented by adjusting pH of the aqueous slurry to higher than 1.2, preferably higher than 1.5. The same purpose is attained also by neutralizing the filtrate separated from the precipitated phthalic acid slurry obtained by extracting naphthoquinone and cooling the phthalic acid solution.

In the treatment, pH should be lower than 5, preferably lower than 3 especially lower than 2.5 optionally lower than 2.2. When the pH is adjusted to this range, the treatment can be carried out without the substantial neutralization of phthalic acid whereby phthalic acid can be effectively recovered. When the pH is adjusted in a range of 3 to 5, the polycondensation of naphthoquinone can be substantially prevented, however a strong acid for an acidic precipitation of a phthalate is required for the recovery of phthalic acid. For example, it is acidified with a strong acid such as sulfuric acid to produce phthalic acid and then, phthalic acid is separated. When pH is higher than 5, large amounts of the base and the acid for the acidic precipitation are required. This is not advantageous in an industrial operation.

An amount of water used in the process of the present invention is large enough to completely dissolve phthalic acid by heating the aqueous slurry at 60° to 110° C. preferably 70° to 100° C. When the pH is lower than 2.5, an amount of water is 7 to 30 times preferably 10 to 20 times by weight of phthalic acid.

As described in Japanese Unexamined Patent Publication No. 9209/1978, when the pH is adjusted to the range for the monosalt of phthalic acid, an amount of water can be decreased depending upon the solubility thereof. The adjustment of pH of the aqueous slurry can be carried out by adding a base or an aqueous solution of a base to the aqueous slurry or a filtrate separated from phthalic acid (mother liquor obtained by separating phthalic acid crystal).

Suitable bases used for adjusting pH include strong alkaline materials such as sodium hydroxide, sodium carbonate; weak alkaline materials such as sodium bicarbonate, disodium phthalate and disodium maleate; and ammonia and amines. In usual, it is preferable to use an aqueous solution of sodium hydroxide or sodium carbonate.

The organic solvent used for the process of the present invention is selected from the group consisting of chain and/or cyclic saturated hydrocarbons which are liquid at the treatment temperature in the extraction. In usual, the organic solvent has a boiling point of higher than 60° C. at the atmospheric pressure and is preferably liquid at the ambient temperature and especially has a boiling point of 80° to 300° C.

When naphthoquinone is recovered by separating the solvent, it is preferable to have a boiling point of lower than 180° C. from the viewpoint of less evaporation loss of naphthoquinone. When the solvent has a boiling point of lower than 60° C. at the atmospheric pressure, the vapor pressure is higher to increase the loss of the solvent and to be difficult for processing it. When the solvent is solid at the ambient temperature, it is difficult to process it in an industrial operation.

Suitable saturated hydrocarbons include straight chain aliphatic hydrocarbons such as n-hexane, n-heptane, n-octane and n-nonane; and branched chain aliphatic hydrocarbons such as isohexane, isoheptane, and isooctane; and cyclic saturated hydrocarbons such as cyclohexane, cycloheptane, cyclooctane or alkyl substituted derivatives thereof and paraffin type kerosin and light oil. A mixture of two or more solvents can be also used.

An amount of the solvent is depending upon the extraction condition, and is more than the amount for dissolving naphthoquinone, and is usually more than 10 times preferably 15 to 50 times by weight of naphthoquinone.

It is preferable to select a desired amount of solvent so as to easily separate by the phase separation from the naphthoquinone solution from the viewpoint of the difference of specific gravity of the aqueous phthalic acid solution.

In the process of the present invention, a temperature for extracting naphthoquinone with a solvent from the aqueous slurry of naphthoquinone and phthalic acid is selected from the range of 60° to 110° C. In the process, the aqueous slurry can be heated to a desired temperature after contacting the solvent with the aqueous slurry before dissolving phthalic acid and the extraction can be also carried out after dissolving phthalic acid.

In order to effectively recover phthalic acid from the aqueous slurry of naphthoquinone and phthalic acid, it is preferable to be higher concentration of phthalic acid. Therefore, the temperature in the extraction is preferably higher. Thus, a polycondensation of naphthoquinone is remarkably high at higher temperature. Therefore, it is preferable to heat after transferring naphthoquinone into the solvent phase by adding the solvent before heating. Thus, the maximum temperature in the extraction is 110° C. On the other hand, when it is lower than 60° C., the solubility of phthalic acid to water or the solubility of naphthoquinone to the solvent is low thereby requiring a large amount of the solvent. This is not advantageous in an industrial operation. Therefore, the temperature in the extraction is selected from a range of 60° to 110° C., preferably a range of 70° to 100° C. In the contact of the solvent with the aqueous slurry, any conventional methods such as continuous or batch methods using a line mixer or a mixing tank can be employed. When the mixing tank is used for the extraction, the mixture is separated into the upper phase of a solution of naphthoquinone and the lower phase of an aqueous solution of phthalic acid and the bottom of resinous materials by keeping at a stand-still after the mixing. The resinous materials are separated and then, the solution of naphthoquinone having high purity is separated from the aqueous solution of phthalic acid. It is also possible to continuously combine the steps of the contact, the heating and the separation.

Figure 3:
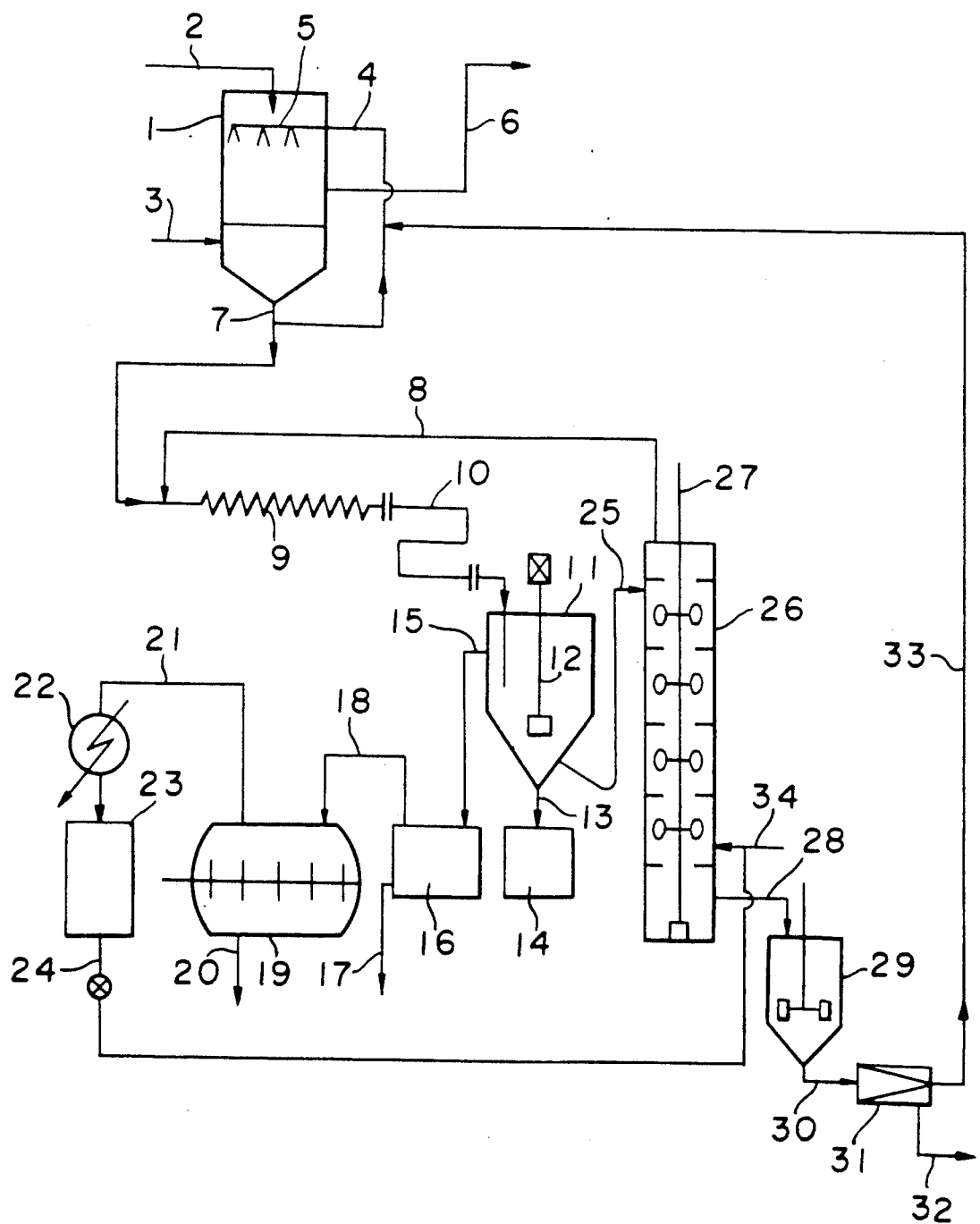
FIG. 3 is a flow diagram of one embodiment of the process of the present invention.

FIG. 3 is a flow diagram of one embodiment of a continuous process of the present invention.

In FIG. 3, the reference numeral (1) designates a scrubber, (2) designates an inlet pipe for feeding the reaction mixture gas formed by the catalytic vapor phase oxidation of naphthalene; (3) designates an inlet pipe for feeding an alkaline material for adjusting pH; (4) designates an inlet pipe for an aqueous medium; (5) designates a showering pipe for the aqueous medium; (6) designates an outlet pipe for an off gas; (7) designates an outlet pipe for an aqueous slurry of naphthoquinone and phthalic acid formed in the scrubber (1); (8) designates an inlet pipe for the saturated hydrocarbon solvent; (9) designates a pipe mixer; (10) designates an extractor of naphthoquinone wherein heating the mixture to a desired temperature; (11) designates a phase separation tank; (12) designates a stirrer; (13) designates an outlet pipe for resinous materials; (14) designates a storage tank for the resinous materials; (15) designates an outlet pipe for the naphthoquinone solution; (16) designates a storage tank for the naphthoquinone solution; (17), (18) respectively represents pipes; (19) designates a vacuum evaporator; (20) designates an outlet pipes for naphthoquinone; (21) designates an outlet pipe for a solvent vapor; (22) designates a condenser; (23) designates a tank for the solvent; (24) designates a pipe for feeding the solvent to extractor column; (25) designates an outlet pipe for the aqueous solution of phthalic acid; (26) designates a counter-current extractor column; (27) designates a stirrer; (28) designates a discharge pipe for the aqueous solution of phthalic acid; (29) designates a tank for crystallizing phthalic acid; (30) designates an outlet pipe for the slurry of crystallized phthalic acid; (31) designates a decantor; (32) designates an outlet pipe for phthalic acid crystal; (33) designates a pipe for discharging the filtrate from the decantor (31) and returning it into the scrubber (1); and (34) designates an inlet pipe for filling up the solvent.

The process for producing naphthoquinone having high purity by this apparatus will be illustrated. The reaction mixture gas formed by the catalytic vapor phase oxidation of naphthalene is fed through the inlet pipe (2) into the scrubber (1). On the other hand, phthalic acid is crystallized from the aqueous solution of phthalic acid and the filtrate (mother liquor) obtained by separating the crystal, is sprayed through the pipe (33) and the inlet pipe (4) and the showering pipe (5) into the scrubber (1) to wash, with water, the reaction mixture gas formed by the catalytic vapor phase oxidation so as to form an aqueous slurry of naphthoquinone and phthalic acid. The alkaline material is added through the inlet pipe (3) to the aqueous slurry so as to adjust pH of the aqueous slurry to 1.2 to 5. The aqueous slurry is continuously fed through the outlet pipe (7) to the pipe mixer (9). A part of the aqueous slurry discharged from the outlet pipe (7) is recycled to the scrubber (1). Into the mixer (9), the saturated hydrocarbon solvent is simultaneously fed through the inlet pipe (8) to mix with the aqueous slurry. The mixture is fed into the extractor (10) for naphthoquinone wherein it is heated at 60° to 110° C. preferably 70° to 100° C. especially 80° to 95° C. whereby 70 to 80 wt. % of naphthoquinone in the aqueous slurry is extracted into the solvent and then the mixture is fed into the phase separation tank (11) wherein the mixture is slowly mixed to perform the phase separation into the upper phase of the saturated hydrocarbon solution of naphthoquinone; the lower phase of the aqueous solution of phthalic acid and the precipitate of the resinous materials which are not dissolved in either the solvent phase or aqueous phase. The precipitate of the resinous materials is passed through the discharge pipe (13) into the storage tank (14) for the resinous materials.

The solution of naphthoquinone as the upper phase in the separation tank (11) is fed through the outlet pipe (15) into the storage tank (16). The solution of naphthoquinone contains only about 1% impurities. The acid content is remarkably smaller than that of naphthoquinone obtained by extracting it with an aromatic hydrocarbon solvent. Therefore, the resulting naphthoquinone can be used as the reagent for the next steps, without a purification. For example, when the naphthoquinone is used for a process for producing anthraquinone by Diels-Alder process, anthraquinone intermediate such as 1,4,4a,9a-tetrahydroanthraquinone or its salt which has high purity can be quantatively obtained. When naphthoquinone is used for such purpose, the solution of naphthoquinone is fed from the storage tank (16) through the pipe (17) into the process for producing such product.

In order to purify naphthoquinone, the solution of naphthoquinone is discharged from the storage tank (16) through the pipe (18) and is fed into the vacuum evaporator (19) wherein the solution is heated with stirring to distil off the solvent to obtain powdery naphthoquinone which is discharged through the discharge pipe (20). On the other hand, the solvent vapor is fed through the outlet pipe (21) into the condenser (22) wherein the vapor is liquefied to be stored in the storage tank (23) for the solvent. When the powdery naphthoquinone is produced by separating the solvent, it is preferable to use a solvent having a boiling point of lower than 180° C. under the atmospheric pressure.

The aqueous solution of phthalic acid discharged from the bottom of the separation tank (11), is fed to the top of the counter-current extractor column (26) at the specific temperature so as to counter-currently contact with the solvent (the solvent stored in the storage tank (23) fed through the pipe (24) and the solvent for filling up by feeding from the inlet pipe (34)) fed from the lower part of the column (26) whereby naphthoquinone remained in the aqueous solution of phthalic acid is completely removed and the aqueous solution is fed through the bottom of the counter-current extractor column (26) into the phthalic acid crystallizing tank, wherein the aqueous solution is cooled to crystallize phthalic acid and the crystal is separated by the decantor (31) and is discharged through the outlet pipe (32). On the other hand, the filtrate discharged from the decantor (19) is recycled through the pipe (33) and the inlet pipe (4) into the scrubber (1). It is possible to adjust pH in the passage for the recycling if necessary. The solvent discharged from the top of the countercurrent extractor column (26) is fed through the inlet pipe (8) for the solvent into the mixer (9).

When pH of the aqueous slurry is adjusted in a range of forming the monosalt of phthalic acid, an aqueous solution of the monosalt of phthalic acid is obtained. When the solution is cooled to crystallize it, the monosalt of phthalic acid crystal is recovered. When an acid is added to the aqueous solution of the monosalt of phthalic acid, phthalic acid is formed and phthalic acid crystal can be obtained by cooling it for the crystallization.

When phthalic anhydride is produced from the resulting phthalic acid, the phthalic acid is dehydrated and distilled by the conventional process.

As described above, naphthoquinone can be used in a form of solution or can be also obtained as powder by concentrating to dry it under a reduced pressure. In accordance with the present invention, naphthoquinone having high purity of higher than 95% preferably 98% such as about 99% can be obtained without a purification step though it has not been attained to produce such pure product in the conventional process.

The present invention will be illustrated by certain examples and references in detail. In the examples, the terms of "part" and "%" mean "part by weight" and "% by weight".

EXAMPLE 1

A reaction mixture gas formed by a catalytic vapor phase oxidation of naphthalene was brought into contact with water to obtain 324 parts of an aqueous slurry containing 10.5 parts of naphthoquinone, 27.5 parts of phthalic acid; 5.6 parts of maleic acid; 5.3 parts of sulfuric acid and water (pH of 1.0). Then, 4% aqueous solution of sodium hydroxide was added to the aqueous slurry to adjust pH to 2.2 at 30° C. and then, 194 parts of n-octane was added to the aqueous slurry and the mixture was heated to 85° C. and stirred for about 5 minutes and then, further slowly stirred for 5 minutes to result in a phase separation into a phase of a solution of naphthoquinone, a phase of an aqueous solution of phthalic acid and a resinous bottom. The aqueous solution of phthalic acid and the resinous bottom were discharged from the bottom to separate the phase of the solution of naphthoquinone. The resinous bottom was further separated from the aqueous solution of phthalic acid. A counter-current extraction of the aqueous solution of phthalic acid with 100 parts of n-octane was carried out. The resulting n-octane solution containing naphthoquinone was combined with the former solution of naphthoquinone and the mixture was washed with hot water and then, the solution was concentrated and dried at 70° C. under 70 Torr to obtain 10.5 parts of naphthoquinone which had a purity of 99.2% and a content of phthalic acid of 0.01%.

REFERENCE 1

In accordance with the process of Example 1 except using 322.4 parts of the aqueous slurry of Example 1 (pH of 1.0) without adjusting pH and using 32.2 parts of o-xylene as the solvent in the extraction, the separation of naphthoquinone was carried out. As a result, 11.0 parts of naphthoquinone having a purity of 90.5% and a content of phthalic acid of 0.3% was obtained.

In accordance with the process of Reference except adjusting pH of the aqueous slurry of Example 1 to 2.2, the separation of naphthoquinone was carried out. As a result, 11.1 parts of naphthoquinone having a purity of 93.5% was obtained.

EXAMPLE 2

4% Aqueous solution of sodium hydroxide was added to 366 parts of the aqueous slurry of Example 1 to adjust pH to 1.8 at 30° C. Then, 151 parts of cyclohexane was added to the aqueous slurry and the mixture was heated to 90° C. under a pressure of nitrogen of 2 kg/cm$^2$ (gauge) and stirred for about 5 minutes and then slowly stirred to result in a phase separation into a phase of a solution of naphthoquinone and a phase of an aqueous solution of phthalic acid and a resinous bottom. In accordance with the process of Example 1, they were respectively separated. As a result, 11.8 parts of naphthoquinone having a purity of 98.5% was obtained.

EXAMPLE 3

4% Aqueous solution of sodium hydroxide was added to 335 parts of the aqueous slurry of Example 1 to adjust pH to 4.5 at 30° C. In accordance with the process of Example 1, the separation of naphthoquinone was carried out. As a result, 10.9 parts of naphthoquinone having a purity of 99.0% was obtained.

Examples and references are provided for purposes of illustration only and are not intended to be limiting the present invention.

We claim:

1. In a process for separation of naphthoquinone from an aqueous slurry prepared by contacting, with an aqueous medium, a reaction mixture gas containing naphthoquinone and phthalic anhydride formed by a catalytic vapor phase oxidation of naphthalene, an improvement characterized in that naphthoquinone having a purity of higher than 95% in a form of a solution or a powder is separated by adjusting the pH of said aqueous slurry to 1.2 to 5 and extracting naphthoquinone with a straight or branched chain saturated hydrocarbon or cyclic saturated hydrocarbon at 60° to 110° C. under the condition of substantially dissolving phthalic acid in the aqueous phase and leaving resinous materials separated as a bottom phase and separating a solvent solution of naphthoquinone.

2. A process for separation of naphthoquinone according to claim 1 wherein said solvent has a boiling point of higher than 60° C. at the atmospheric pressure.

3. A process for separation of naphthoquinone according to claim 1 wherein said solvent is used at an amount of more than the amount for dissolving naphthoquinone.

4. A process for separation of naphthoquinone according to claim 1 wherein said solvent is n-hexane, n-heptane, n-octane, n-nonane, isohexane, isoheptane, isooctane, cyclohexane, cycloheptane, cyclooctane or alkyl substituted derivatives thereof and paraffin type kerosin and light oil.

5. A process for separation of naphthoquinone according to claim 1 wherein said extraction is carried out at 70° to 100° C.

6. A process for separation of naphthoquinone according to claim 1 wherein the pH of said aqueous slurry is adjusted to 1.2 to 5 by adding a base to a mother liquor obtained by separating phthalic acid crystals from the aqueous phase and recycling.

* * * * *

UNITED STATES PATENT AND TRADEMARK OFFICE
CERTIFICATE OF CORRECTION

PATENT NO. : 5,153,339

DATED : October 6, 1992

INVENTOR(S) : Ryo Matsuura et al.

It is certified that error appears in the above-identified patent and that said Letters Patent is hereby corrected as shown below:

On Title Page, Item [75], Inventors, the fourth inventor's information should be deleted. The inventors' information should read as follows:

--Ryo Matsuura, Yamato; Tatsuyoshi Komatsu, Kamakura; Kenji Usui, Tokyo, all of Japan--.

Signed and Sealed this

Fifth Day of October, 1993

*Attest:*

BRUCE LEHMAN

*Attesting Officer*     *Commissioner of Patents and Trademarks*